United States Patent [19]
Fowler, Jr.

[11] Patent Number: 5,964,697
[45] Date of Patent: Oct. 12, 1999

[54] SURGICAL RETRACTOR STAY APPARATUS

[75] Inventor: James M. Fowler, Jr., Houston, Tex.

[73] Assignee: Lone Star Medical Products, Inc., Houston, Tex.

[21] Appl. No.: 09/067,125

[22] Filed: Apr. 27, 1998

Related U.S. Application Data

[63] Continuation of application No. 08/635,746, Apr. 22, 1996, abandoned.

[51] Int. Cl.$^6$ ...................................................... A61B 11/02
[52] U.S. Cl. ............................................ 600/210; 600/217
[58] Field of Search ..................................... 600/206, 210, 600/211, 213–215, 226, 227, 231, 233, 234

[56] References Cited

U.S. PATENT DOCUMENTS

| | | | |
|---|---|---|---|
| 3,515,129 | 6/1970 | Truhan | 128/20 |
| 3,542,015 | 11/1970 | Steinman | 600/206 X |
| 3,749,088 | 7/1973 | Gauthier | 600/206 |
| 3,762,401 | 10/1973 | Tupper | 128/20 |
| 4,049,987 | 9/1977 | Hurson | 600/206 |
| 4,185,636 | 1/1980 | Gabbay et al. | 128/334 R |
| 4,190,042 | 2/1980 | Sinnreich | 600/206 X |
| 4,254,763 | 3/1981 | McCready et al. | 128/20 |
| 4,257,406 | 3/1981 | Schenk | 128/20 |
| 4,263,900 | 4/1981 | Nicholson | 128/20 |
| 4,274,398 | 6/1981 | Scott, Jr. | 128/20 |
| 4,321,916 | 3/1982 | McKee | 128/20 |
| 4,337,762 | 7/1982 | Gauthier | 128/20 |
| 4,337,763 | 7/1982 | Petrassevich | 128/20 |
| 4,344,420 | 8/1982 | Forder | 128/20 |
| 4,355,631 | 10/1982 | LeVahn | 128/20 |
| 4,380,999 | 4/1983 | Healy | 128/20 |
| 4,387,706 | 6/1983 | Glass | 128/20 |
| 4,412,532 | 11/1983 | Anthony | 128/20 |
| 4,421,107 | 12/1983 | Estes et al. | 128/20 |
| 4,421,108 | 12/1983 | Cabrera et al. | 128/20 |
| 4,430,991 | 2/1984 | Darnell | 128/20 |
| 4,434,791 | 3/1984 | Darnell | 128/20 |
| 5,080,088 | 1/1992 | LeVahn | 600/206 |
| 5,231,974 | 8/1993 | Giglio et al. | 600/206 |
| 5,245,987 | 9/1993 | Redmond et al. | 600/204 |
| 5,307,805 | 5/1994 | Byrne | 600/227 X |
| 5,769,783 | 6/1998 | Fowler | 600/226 |

FOREIGN PATENT DOCUMENTS

| | | |
|---|---|---|
| 1222141 | 2/1971 | United Kingdom . |
| 1550254 | 8/1979 | United Kingdom . |
| 1550255 | 8/1979 | United Kingdom . |

*Primary Examiner*—Richard J. Apley
*Assistant Examiner*—Denise Pothier
*Attorney, Agent, or Firm*—Akin, Gump, Strauss, Hauer & Feld, L.L.P.

[57] ABSTRACT

A surgical retractor for use in performing surgery upon a patient at a surgical siting includes an annular frame conformed to fit the surface of the patient's body at the site, the frame having a plurality of notches, each having a width. A plurality of stays are provided each including an elongated elastic member having a length, a width, and proximal and distal end portions. The width of each elastic member is preferably greater than the width of the notches so that the stay forms a connection with the annular frame by engaging a selected portion of the elastic member into a notch. At least a portion of one of the elastic members includes a section of hollow elastic tubing having a bore surrounded by a tubing wall. A tissue holding member includes a handle plate forming a first plane, the plate having a thickness, a length, and a height. A wide section of the tissue holding member is much wider than the diameter of the tubing. The wide section defines a second plane that this generally perpendicular to the first plane. The wide section has left and right opposed edge portions and a plurality of curved hooks extend from the wide section and include at least a pair of hooks positioned at the opposed edge portions of the wide section.

12 Claims, 1 Drawing Sheet

SURGICAL RETRACTOR STAY APPARATUS

This is a continuation application of application Ser. No. 08/635,746, filed Apr. 22, 1996 abandoned.

BACKGROUND OF THE INVENTION

1. Field of the Invention

The present invention relates to surgical retractors and surgical retractor stays. More particularly, the present invention relates to an elastic surgical retractor stay that includes a narrow flange-like handle, a transition section, and a wide portion carrying multiple spaced apart hooks for deep tissue retracting.

2. Description of the Related Art

During the course of a surgical procedure or operation, the surgeon opens the patient with a scalpel to form an incision. As the surgeon cuts deeper, the operating room staff typically holds tissue away from the operative field using retractors.

Most retractors are one piece metallic implements that retract a wound in a non-yielding manner. Manipulation and movement of the surgeon as well as movement caused by contracting muscles or tissues of the patient can result in bruising or tearing of tissue.

Once an incision is separated and retracted, there is often a need for multiple stays in the form of sutures for holding various tissues for example different organs. Elastic surgical retractor systems are in commercial use that include Multiple elastic stays each having an elongated elastic member that is typically a hollow length of elastic tubing. The elastic tubing provides proximal and distal end portions. The distal end portion carries an elongated hook constructed of wire. This wire hook is placed in the distal end of the bore of the hollow tubing. A shrink wrap can be placed over the hook to hold it firmly in position within the bore of the tubing at the distal end. The embedded portion of the hook member is usually recurved to form a handle. Such wire hook type surgical retractors have been successful in retracting skin tissues. However, very large tissue groups that are deep within the body cavity must still be held with manual and non-yielding retractors. An example of deep tissue retractors are those sold for example by Aesculap. These include some elongated instruments that have handles and/or circular openings that can receive a user's hand, thumb or finger. Many of these retractors have a series of parallel hooks that can be blunt, semi-sharp or sharp. Aesculap sells such handle held non-yielding retractors with two, three, four, six and eight hooks that are part of an integral rigid retractor having an elongated shaft and handles. These retractors are also sold under the terms "Kosher and Volkmann". They are commercially available from Aesculap and other medical companies. These retractors fail to provide a yielding deep retraction system that has utility for the retraction of deep tissues and large tissue groups such as muscles, ligaments, tendons, and fatty tissues.

Various patents have issued for yielding retractor stay systems. A surgical retractor array system is disclosed in U.S. Pat. No. 4,434,791, issued to W. Dale Darnell on Mar. 6, 1984. This surgical retractor system comprises an array of standardized, interchangeable, annular retractor frame sections of various shapes of which the end portions are configured to permit the interchangeable, hinged connection of the various shaped frames in forming generally annular retractor units adaptable to conform to fit the surface contours of various patients upon which a surgical operation is to be performed.

Other recent patents have issued that relate to elastic type retractor stays and related retractor frames and systems.

U.S. Pat. No. 4,274,398, issued to Frank B. Scott, Jr., issued Jun. 23, 1981, discloses a surgical retractor which includes an annular frame conformed to fit the surface contour of the portion of the body to be operated on. At least one stay includes an elastic member and a tissue holding hook. The frame has a plurality of notches spaced about its periphery. The elastic member of the stay is adapted to be inserted into one of the notches and held in place by friction to retract the tissue. The hook is a single, curved wire member that is anchored at its distal end to a plug-like body. Retractor stays of this type have been successful in retracting skin and related surface tissue but suffer when retracting larger and deeper masses of tissue such as fatty tissues, muscle, tendons and ligaments deep within a body cavity.

U.S. Pat. No. 4,430,991, issued to W. Dale Darnell, issued on Feb. 14, 1984, discloses a surgical retractor stay with a single tissue holding hook affixed to the elastic hollow tubing member of the stay by a retaining member. The retaining member has a body in which the hook shank is embedded with the sharp end of the hook extending from one end of the body. A stud with a tapered knob on its outer end extends outwardly from the other end of the retaining member body. The size and configuration of the knob and stud enable them to be tightly retained within an end portion of the hollow tubing that is stretchingly installed thereover. A surgical tube connector for joining a pair of hollow elastic surgical tube members having an elongated stud with tapered knobs at each end in which the stud and knobs are dimensioned for tight fitting containment within the end portions of the hollow tube members stretchingly installed thereover.

SUMMARY OF THE INVENTION

The present invention provides an improved surgical retractor system for use in performing surgery upon a portion of a patient's body at a surgical site.

The apparatus includes an annular frame conformed to fit the surface of the patient's body of the surgical site. The frame provides a plurality of notches, each having a width.

A stay includes an elongated elastic member having a length, a width, and proximal and distal ends, wherein the width of each elastic member is greater than the width of the notches.

At least a portion of one end of the elastic member includes a section of hollow elastic tubing having a bore surrounded by a tubing wall.

A tissue holding member includes a handle forming a first plane, the handle having a thickness, a length, and a height. The tissue holding member includes a transitional section that is a smaller thickness section having the thickness that approaches that of the handle.

A wide section is much thicker than the diameter of the tubing. The wide section includes left and right preferably parallel edge portions.

A plurality of hooks extend from the wide section, including at least a pair of hooks positioned at said opposed parallel edge portions of said wide section.

In the preferred embodiment, the handle plate is a solid plate member having proximal and distal end portions, a lower edge, and an upper edge, the distal portion of the handle extending beyond the distal end of said elastic member.

In the preferred embodiment, the handle plate has proximal and distal end portions wherein the distance between the upper and lower edges gradually increases beginning at the proximal end of the handle plate to a position at least half way in between the proximal and distal ends of the handle plate.

The handle plate preferably has a generally uniform thickness between the proximal and distal ends, but a height between the upper and lower edges that varies.

The wide section has a thickness that is preferably at least about 3 times the diameter of the elastic member. In the preferred embodiment, a pair of hooks are spaced apart, extending from the parallel edges of the wide section of the tissue holding member. In another embodiment, a plurality of four hooks extends from the wide section of the tissue holding member. Any multiple hooks such as three, six, or eight hooks could extend from the wide section.

The upper edge of the handle plate can include a pair of inclined portions that aid in assembly of the plate to the bore of the elastic member.

The height of the handle plate is greater than the diameter of the hollow bore of the elastic tubing.

The handle plate has a height between the upper and lower edges that is preferably greater than the external diameter of the elastic member.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
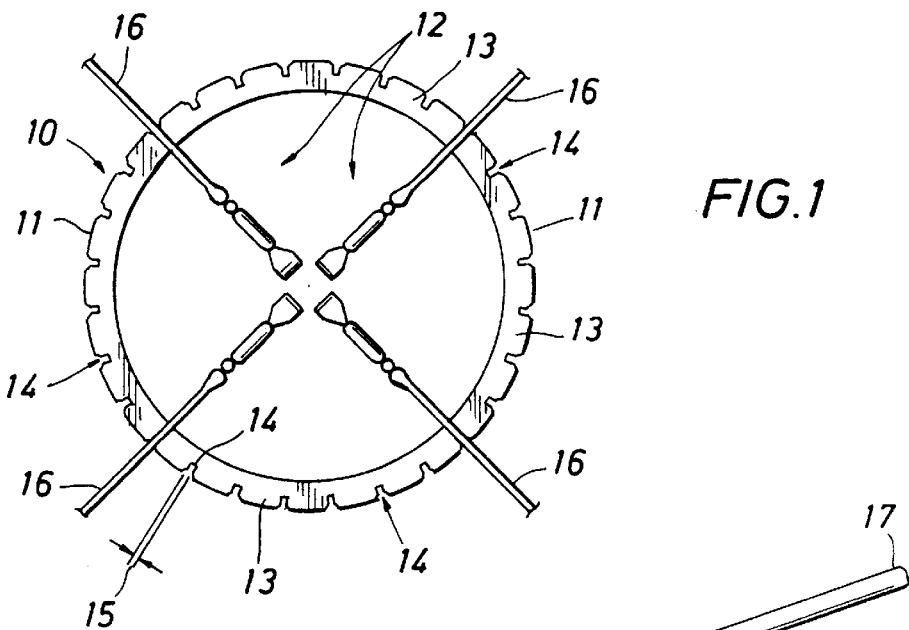
FIG. 1 is a plan view of the preferred embodiment of the apparatus of the present invention.

FIG. 1 shows generally the preferred embodiment of the apparatus of the present invention designated generally by the numeral 10.

In FIG. 1, there can be seen an annular frame 11 having an open center 12. Frame 11 can be constructed of metal or plastic for example. The frame 11 comprises a peripheral flange member 13 that can be ell or angle shaped in cross section. The peripheral flange 13 has a plurality of notches 14 each having a notch width 15.

Figure 2:
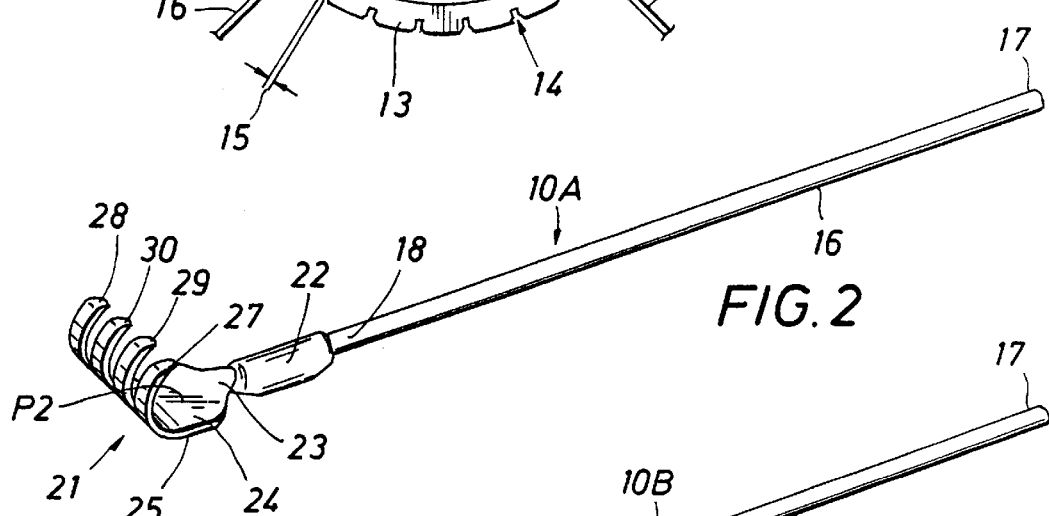
FIG. 2 is a perspective view of the preferred embodiment of the apparatus of the present invention showing a four hook surgical retractor stay.
Figure 3:
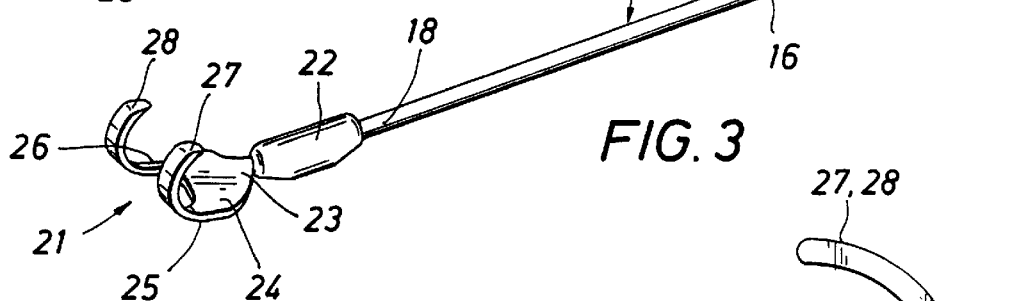
FIG. 3 is a perspective view of the preferred embodiment of the apparatus of the present invention showing a two hook surgical retractor stay.

The notches 14 receive the elastic member 16 portion of a surgical retractor stay 10A (FIG. 2) or 10B (FIG. 3). In FIGS. 2–3, surgical retractor stay 10A and 10B includes an elongated elastic member 16 having a proximal end portion 17 and a distal end portion 18. Each elastic member 16 is preferably cylindrically shaped having a cylindrical outer surface 19 and a hollow bore 20.

Figure 4:
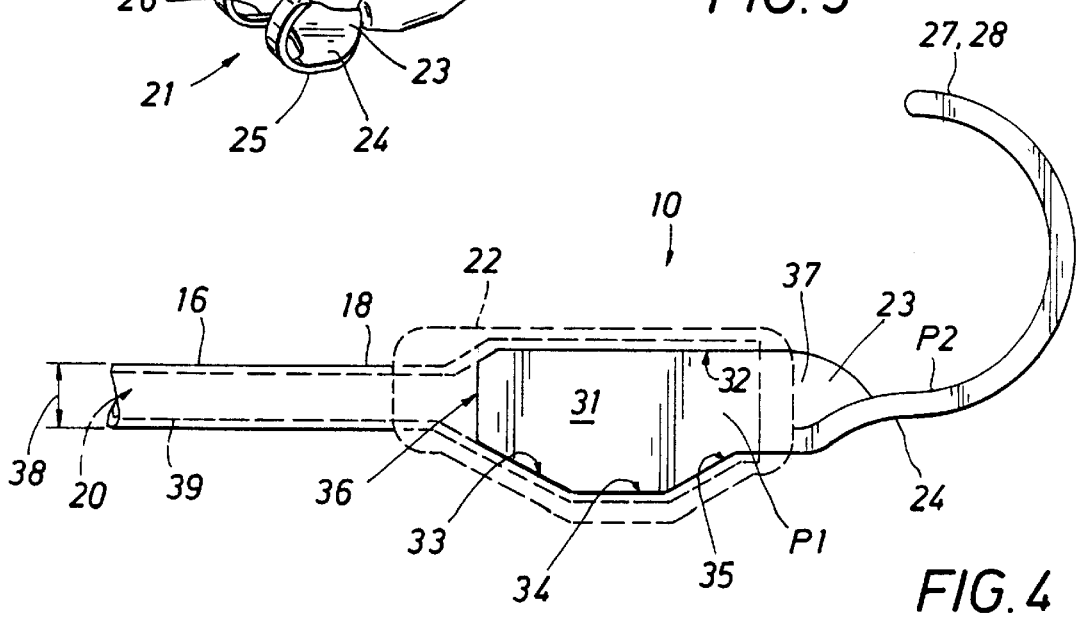
FIG. 4 is a partial sectional view of the preferred embodiment of the apparatus of the present invention.

A tissue holding member 21 is affixed to distal end 18 of elastic member 16 in FIGS. 2 and 4. The tissue holder member 21 as shown in FIG. 4 is attached at handle plate 31 to the bore 20 of elastic member 16. Tissue holding member 21 includes handle sheath 22, transition section 23, and wide section 24. Wide section 24 has a pair of opposed, preferably parallel edges 25, 26. A curved hook 27, 28 extends from each edge 25, 26 as shown in FIGS. 2 and 4.

Handle plate 31 is shown in more detail in FIG. 4. Handle plate 31 forms a first plane P1 and wide section 24 defines a second plane P2 with the first and second planes being generally transverse to one another. Handle plate 31 has a lower linear edge 32, a pair of inclined edges 33, 35 and an edge 34 that is parallel to edge 32. The edges 33, 34, 35 comprise an upper edge that is opposite lower edge 32. Handle plate 31 also includes proximal end 36 and distal end 37. A variable height is provided to handle plate 31 in between lower edge 32 and the upper edge that is a combination of inclined edges 33, 35 and parallel edge 34. The variable height of handle plate 31 aids in the assembly of handle plate 31 to elastic member 16 more particularly to the bore 20 thereof.

The height of handle plate 31 is much greater than the internal diameter of bore 20 of elastic member 16. In FIG. 4, the height of plate 31 is designated as 38. This allows a very tight connection to be formed between elastic member 16 and handle plate 31. In the preferred embodiment, the distal end 37 of handle plate 31 extends beyond the extreme distal end 18 of elastic member 16.

In order to assemble tissue holding member 21 to elastic member 16, proximal end 36 of handle plate 31 enters the bore 20 of elastic member 16 at distal end 18 of elastic member 16. The inclined surface 33 enables the tubing wall 39 of elastic member 16 to stretch. Bore 20 is gradually enlarged until distal end 18 reaches parallel edge 34. The parallel edge 34 is positioned at the maximum height of handle plate 31. Inclined surface 35 allows the tubing 16 to constrict at distal end 18 of tubing 16. Handle sheath 22 can then be used to encapsulate the connection between elastic member distal end 18 and handle plate 31. Sheath 22 can be heat shrink tubing of plastic.

The method of the present invention allows deep tissue such as muscle, fatty tissue, tendons, and ligaments to be retracted in a yielding fashion, providing an improvement over the prior art. Further, "fishhook" style stays can be used to retract surface tissues, with the deep tissues then being retracted by the retractor stay apparatus 10 according to the invention. Further, the surgical retractor stay apparatus 10 of the present invention allows very wide retractor tissue holding members to be employed with relatively smaller diameter elastic members. In the preferred embodiment, the tissue holding members 21 have a width between edges 25 and 26 that is at least 3 times greater than the outer diameter of elastic member 16.

The following table lists the parts numbers and parts descriptions as used herein and in the drawings attached hereto.

| PARTS LIST | |
|---|---|
| Part Number | Description |
| 10 | surgical retractor stay apparatus |
| 10A | surgical retractor stay |
| 10B | surgical retractor stay |
| 11 | annular frame |
| 12 | central opening |
| 13 | peripheral flange |
| 14 | notch |
| 15 | notch width |
| 16 | elastic member |

-continued

PARTS LIST

| Part Number | Description |
| --- | --- |
| 17 | proximal end |
| 18 | distal end |
| 19 | cylindrical wall |
| 20 | hollow bore |
| 21 | tissue holding member |
| 22 | handle sheath |
| 23 | transition section |
| 24 | wide section |
| 25 | edge |
| 26 | edge |
| 27 | nook |
| 28 | nook |
| 29 | nook |
| 30 | hook |
| 31 | handle plate |
| 32 | lower edge |
| 33 | inclined edge |
| 34 | parallel edge |
| 35 | inclined edge |
| 36 | proximal end |
| 37 | distal end |
| 38 | height |
| 39 | tubing wall |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgical retractor apparatus for use in performing surgery upon a portion of a patient's body at a surgical site, comprising:
   a) a frame conformed to fit the surface of the patient's body at a surgical site, said frame having a plurality of notches, each said notch having a width;
   b) a stay that removably attaches to said frame at one of said plurality of notches, wherein said stay includes an elongated elastic member having a length, a width, and proximal and distal ends;
   c) wherein the width of said elastic member is greater than the width of said notches so that said elastic member can be secured at a position in between said ends to said notch;
   d) at least a portion of one of said ends said elastic member including a section of hollow elastic tubing having a bore surrounded by a tubing wall;
   e) said stay having a tissue holding member that comprises:
   a handle plate forming a first plane, said handle plate having a generally uniform thickness, a length, and greater than the bore diameter;
   a wide plate section that is thicker than the diameter of said tubing, said wide plate section defining a second plane generally transverse to the first plane and having left and right opposed edge portions;
   a transitional section that connects said handle plate with said wide plate section, and having a smaller thickness portion having a thickness that approaches the thickness of said handle plate; and
   a plurality of hooks extending from said wide plate section and including at least a pair of hooks positioned at said opposed edge portions of said wide plate section.

2. The surgical retractor apparatus of claim 1 wherein said frame is annular with a central opening.

3. The surgical retractor apparatus of claim 1 wherein said handle plate has proximal and distal end portions, a lower edge, an upper edge, and said distal end portion extends beyond said distal end of said elastic member.

4. The surgical retractor apparatus of claim 3 wherein the distance between the upper and lower edges gradually increases beginning at said proximal end portion of said handle plate and reaches a maximum distance approximately half way between said proximal and distal end portions of said handle plate.

5. The surgical retractor apparatus of claim 3 wherein said handle plate has a generally uniform thickness between said proximal and distal end portions and the distance between said upper and lower edges varies.

6. The surgical retractor apparatus of claim 3 wherein said handle plate includes a linear lower edge.

7. The surgical retractor apparatus of claim 3 wherein said upper edge of said handle plate has a pair of inclined portions.

8. The surgical retractor apparatus of claim 3 wherein said handle plate has a height between said upper and lower edges that is greater than the external diameter of said elastic member.

9. The surgical retractor apparatus of claim 1 wherein said wide plate section has a thickness that is approximately 3 times the diameter of said elastic member.

10. The surgical retractor apparatus of claim 1 wherein said elastic member hollow bore has a diameter that is larger than the thickness of said handle plate and the height of said handle plate is greater than the hollow bore diameter.

11. An elastic surgical retractor stay apparatus for use in performing surgery at a surgical site with an incision, comprising:
   a) a stay that includes an elongated elastic member having a length, a width, and proximal and distal ends;
   b) wherein a proximal end portion of said stay attaches to a frame and holds said proximal end of said stay at a location away from the incision;
   c) at least a portion of one of said ends of said elastic member including a section of hollow elastic tubing having a tubing diameter and a bore with a bore diameter surrounded by a tubing wall; and
   d) said stay having a tissue holding member for holding and retracting tissue at the incision, wherein said tissue holding member comprises:
   a handle plate having a first generally planar surface, said plate having a thickness, a length, and a height that is greater than the bore diameter;
   a wide section that is thicker than the tubing diameter, said wide section having a second generally planar surface generally transverse to the first generally planar surface and having left and right opposed edge portions;
   a transitional section that connects said handle plate with said wide section, and having a smaller thickness portion with a thickness that approaches the thickness of said handle plate; and
   a plurality of hooks extending from said wide section and including at least a pair of hooks positioned at said opposed edge portions of said wide section.

12. A surgical retractor for use in performing surgery upon a portion of a patient's body at a surgical site, comprising:
   a) a stay that includes an elongated elastic member having a length, a width, and proximal and distal ends;
   b) an anchor removably connected to said proximal end for anchoring said proximal end of said stay at a location spaced from the surgical site;

c) at least a portion of one said end of said elastic member including a section of hollow elastic tubing having a bore surrounded by a tubing wall; and d) said stay having a tissue holding member that comprises:

a handle plate having a first generally planar surface, said plate having a thickness, a length, and a height that is greater than the bore diameter;

a wide plate section that is thicker than the diameter of said tubing, said wide plate section having a second generally planar surface generally transverse to the first generally planar surface and having left and right opposed edge portions;

a transitional section that connects said handle plate with said wide plate section, and having a smaller thickness portion with a thickness that approaches the thickness of said handle plate; and a plurality of hooks extending from said wide plate section and including at least a pair of hooks positioned at said opposed edge portions of said wide plate section.

\* \* \* \* \*